United States Patent [19]

Maruyama et al.

[11] 3,985,621

[45] Oct. 12, 1976

[54] STOPPING AGENTS FOR ENZYME REACTIONS OF DEHYDROGENASE SYSTEMS

[75] Inventors: Motohiro Maruyama; Keiko Yamamoto, both of Tokyo, Japan

[73] Assignee: Sankyo Company Limited, Tokyo, Japan

[22] Filed: Oct. 21, 1975

[21] Appl. No.: 624,557

[30] Foreign Application Priority Data

Oct. 23, 1974    Japan.............................. 49-122243

[52] U.S. Cl............................. 195/103.5 R; 424/12
[51] Int. Cl.²........................................... C12K 1/00
[58] Field of Search................ 195/103.5 R; 424/12, 424/7

[56]    References Cited
        UNITED STATES PATENTS 3,838,010    9/1974    Hammer...................... 195/103.5 R
3,899,397    8/1975    Morin et al.................. 195/103.5 R Primary Examiner—A. Louis Monacell
Assistant Examiner—Robert J. Warden
Attorney, Agent, or Firm—Toren, McGeady and Stanger

[57]              ABSTRACT

New application of an aqueous alkali solution of cyclohexylaminopropanesulfonic acid, said acid being contained therein with a specific range of concentration and said solution having a specific range of pH value, as a stopping agent for stopping an enzyme reaction of a dehydrogenase or a dehydrogenase system in a spectrophotometric assay method of an activity of serum enzyme in said enzyme or enzyme system.

24 Claims, No Drawings

STOPPING AGENTS FOR ENZYME REACTIONS OF DEHYDROGENASE SYSTEMS

This invention relates to a reaction stopping agent utilizable for the measurement of activity of serum enzymes which are thought of markers for diagnosis of liver, heart and muscle diseases in human beings.

More specifically, it is concerned with a new application or use of an aqueous alkali solution of cyclohexylaminopropanesulfonic acid having specified ranges of the concentration and pH value thereof as a stopping agent for stopping an enzyme reaction of a dehydrogenase or a dehydrogenase system in a spectrophotometric assay method of an activity of serum enzyme in the above enzyme or enzyme system.

Still more particularly, it is concerned with a method for stopping an enzyme reaction of a dehydrogenase or a dehydrogenase system in a spectrophotometric assay method of an activity of serum enzyme in said enzyme or enzyme system which comprises applying as a stopping agent for said enzyme reaction an aqueous alkali solution of cyclohexylaminopropanesulfonic acid having a concentration of 0.1 – 2M and a pH value of 10.5 – 12.5.

In the spectrophotometric assay method of an activity of serum enzyme in a dehydrogenase or a dehydrogenase system which may be used in this invention, there may be included various assay methods commonly employed in the art for such purposes, for instance, an ultraviolet absorbance assay method (hereinafter referred to as "ultraviolet assay method") wherein an activity of glutamic — oxaloacetic transaminase (hereinafter referred to as GOT), glutamic - pyruvic transaminase (hereinafter referred to as GPT), aldolase (hereinafter referred to ALD), creatinephosphokinase (hereinafter referred to as CPK), lactic dehydrogenase (hereinafter referred to as LDH), alcohol dehydrogenase or sorbitol dehydrogenase in human serum is determined by measuring an absorbance change at 340nm of nicotinamide-adenine dinucleotide (hereinafter referred to as NAD) or nicotinamide adenine dinucleotide phosphate (hereinafter referred to as NADP) added in the reaction medium either alone or in combination with an appropriate dehydrogenase (system); a fluorometric assay method (hereinafter referred to as "fluorometric assay method") wherein a serum enzyme activity of the above-mentioned enzymes in human serum is determined by measuring a change in fluoroescence intensity of NAD or NADP excited with 340nm beam, said NAD or NADP being added to a reaction medium either alone or in combination with a dehydrogenase; and the like.

This invention will be more fully disclosed with particular reference to the ultraviolet assay method for convenience' sake, but it should be noted that the stopping agent of this invention is satisfactorily applicable to other assay methods such as the fluorometric assay method and so on.

Increase in the GOT or GPT activity in serum occurs along with some liver diseases or coronary heart infraction, then measurement of the activity is considered useful for diagnosis of these diseases.

For measuring serum GOT or GPT activity, the reaction can be carried out through addition of malic dehydrogenase to the reaction medium in case of GOT and LDH in case of GPT, together with the enzyme substrates such as α-ketoglutaric acid and L-aspartic acid for the former enzyme or α-ketoglutaric acid and L-alanine for the latter, and a reduced form of NAD (hereinafter referred to as NADH) in either case. Oxaloacetic acid derived from aspartic acid with GOT (in case of GPT, pyruvic acid derived from alanine, the GPT case being hereinafter referred to in the parenthesis) is converted to malic acid (lacetic acid) with malic dehydrogenase (lactic dehydrogenase) and NADH concurrently with oxidation of NADH to NAD, which results in decrease of absorbance at 340nm arising from NADH. An amount of the oxaloacetic acid (pyruvic acid) produced by GOT (GPT) is stoichiometrically equal to that of the NADH to be oxidized and a GOT (GPT) activity can be, therefore, determined from an oxidized amount of NADH which is obtained from an absorbance decrease at 340nm.

ALD activity in serum is raised in case of liver diseases, progressive muscular dystrophy or coronary heart infarction.

In measuring ALD activity, one can carry out by adding to a reaction medium fructose-1,6-diphosphate which is a substrate, togethe with triose phosphate isomerase (hereinafter referred to as TMI) and glycerol-1-phosphate dehydrogenase (hereinafter referred to as GDH). In this system, the products by ALD are converted to dioxyacetone phosphoric acid, which is then converted to glycerol-1-phosphate by the action of GDH and NADH. NADH is simultaneously oxidized to NAD. Hydrolysis of 1 mole of fructose-1,6-diphosphate with ALD results in oxidation of 2 moles of NADH.

CPK in serum is increased along with injury of skeletal muscle or heart muscle. For determination of CPK activity, creatine phosphoric acid and adenosine-5'-diphosphate (hereinafter referred to as ADP) are employed as substrates and further hexokinase (hereinafter referred to as HK), glucose, glucose-6-phosphate dehydrogenase (hereinafter referred to as G6PDH) and NADP are added to the reaction medium. By the action of CPK, ADP is converted to adenosine-5'-triphosphate (hereinafter referred to as ATP), while glucose in the reaction medium is converted to glucose-6-phosphate by the action of the ATP and HK. Thereafter, the glucose-6-phosphate is converted to 6-phosphogluconic acid by the action of G6PDH and NADP and NADP is converted to a reduced form of NADP (hereinafter referred to as NADPH), along with the conversion, which results in increased absorbance at 340nm. The ATP amount produced by CPK is stoichiometrically equal to that of NADP to be reduced.

In case of other serum enzymes than those as named above, similar reaction system is employable. In case of a serum enzyme itself being a dehydrogenase as LDH, an enzyme activity is determined by direct dehydrogenation of NADH or NADPH with a substrate so as to change absorption intensity at 340nm.

As stated above, an ultraviolet assay method has a characteristic in that measurements can be effected by the use of a dehydrogenase reaction to couple the reaction of aforementioned serum enzyme with oxidation reaction of NADH (or NADPH) or reduction reaction of NAD (or NADP) in every case.

An ultraviolet assay method does not require coloring procedures and can be effected by extremely simple determination procedures, differing from other assay methods wherein colorimetric determination should be made after coloration of the reaction product or residual substrate.

An absorption intensity of NADH or NADPH at 340nm is also completely proportionable to a concentration thereof and a molar extinction coefficient is sufficiently high. Remarkably high precision, accuracy and reproducibility is obtainable by the ultraviolet assay method, as compared with other known methods. Indication of an activity value (unit), which has been recently recommended by The International Union of Biochemistry, is easily available by multiplying change in absorbance at 340nm by a coefficient. In view of the additional advantage as mentioned just above, an ultraviolet assay method previously applied in a basic biochemical research has been ultimately expected to become practicable in routine assay of serum enzymes in a clinical diagnostic laboratory.

However, the prior ultraviolet assay methods which are manually worked have not yet been widespread, since it is difficult to assay a large number of serum samples owing to impracticability of a stopping agent useful for the abovementioned enzyme reaction and, in case where many serum samples are to be daily determined as done in a clinical diagnostic laboratory, a specific photometer developed particularly for an ultraviolet assay method should be employed, for example, such apparatus as LKB-8600 type Reaction Rate Analyzer (LKB Co., Sweden), Rotochem II Fast Analyzer (Aminco Co., U.S.A.) and so on. More specifically, the ultraviolet assay method in manual procedures employing a conventional photometer is conducted by placing a reaction mixture and a serum sample into a cell and measuring change with time of absorbance at 340nm over 10 – 30 minutes, while according to this time consuming method the number of serum samples to be tested per day is limited to at most 10 – 20 and an operator is very tired with all day working for measurement. Moreover, the above-mentioned specific photometer is a highly expensive apparatus with a cost of ten million – thirty million yen and, therefore, it is not prevalent to middle and small clinical diagnostic laboratories.

In the art, there have been proposed a considerable number of stopping agents for ordinary enzyme reaction, but they are not utilizable for the ultraviolet assay method from the following reasons. Deproteinizing agents such as trichloroacetic acid, perchloric acid, methaphosphoric acid, sulfuric acid — tungstenic acid and the like make disappeared absorption of NADH (or NADPH) at 340nm and other acids, when incorporated in an amount to stop the reaction, make disappeared absorption at 340nm. On the other hand, when an aqueous solution of alkali such as sodium hydroxide is added in an amount to stop the reaction, absorption of NAD (or NADH) at 340nm is apt to change irregularly. If the enzyme reaction is stopped by heat treatment, the reaction mixture becomes turbid owing to serum protein and ordinary centrifugation of 3000 r.p.m. or lower can only remove turbidity partially and not provide a clear solution for measurement.

It is also reported in the art that an aqueous alkali solution of p-chloromercurybenzoate is applicable as a stopping agent for dehydrogenase reaction (E. Raabo, Scandinavian Journal of Clinical & Laboratory Investigation, 17, (1965), 265). However, this solution has been confirmed to give inhibition of dehydrogenase reaction only in case of restricted buffer concentration of a reaction mixture and further to give only partial inhibition of dehydrogenase reaction in case of using a reaction mixture of commercially available diagnostic kits. Then, the prior solution seems to be of no practical use.

As a result of our earnest studies to supply deficiencies of such stopping agents, it has been found that a wide variety of dehydrogenases can be completely inhibited by the use of an appropriate amount of an aqueous alkali solution having a specific concentration of cyclohexylaminopropanesulfonic acid (hereinafter referred to as CAPS) and a specific pH value to show a strong buffer action within an alkaline pH range which does not cause changes in absorption of NAD or NADP around 340nm and also that the present stopping agent has ideal characteristics as a stopping agent, without any influence on turbidity of serum of normal healthy human beings as well as of lipemic serum. This invention has been completed upon the above findings.

It is, accordingly, a primary object of this invention to provide a new method for stopping an enzyme reaction of a dehydrogenase or a dehydrogenase system in a spectrophotometric assay method by the use of an aqueous alkali solution of CAPS.

Other objects and advantages of this invention will become apparent from the following descriptions.

By the use of the present stopping agent, it becomes feasible to conduct simultaneous reactions of many serum samples, stop the rection by addition of the stopping agent after a given period of time and then determine an enzyme activity by measuring absorption at 340nm. According to such procedures, it is feasible to determine the respective activities of 100 – 200 serum samples per day by one operator. In case where an activity is to be determined with lapse of time in a cell, it is impossible to reduce a volume of the reaction mixture to a given one due to necessity for a cell capacity, whereas it is possible, according to the procedures which use the present stopping agent, that an amount of the reaction mixture to be reacted is reduced by adjusting an amount of the stopping agent to be added, as it is sufficient that the final volume after addition of the stopping agent is beyond the necessary capacity for measuring. In general, it is easy to reduce the volume of a reaction mixture so small as 1/3 – 1/6 of the conventional manual method. A blank test for serum can be performed without addition of the reaction mixture and a reagent blank is determined separately. A blank value for the assay is estimated as a sum of the above both blank values. Thus, the reagent is not wasted for such blank correction, which meets requirements from clinical laboratory to save an amount of the reagent.

The findings which are concerned with the present invention and the present method will be more illustratively explained hereinbelow.

1. INHIBITORY ACTION OF AN ALKALINE BUFFER SOLUTION ON DEHYDROGENASE ACTIVITY AND INFLUENCE ON ABSORPTION INTENSITY OF COENZYME AT 340NM.

As a result of our studies on phosphates buffer solution, glycine buffer solution, arginine buffer solution, guanidine buffer solution, and CAPS buffer solution, it has been found that other buffer solutions than CAPS buffer solution have some drawbacks and are unable to be utilized as a stopping agent.

Phosphate buffer solution has an action to promote autoxidation of NADH remarkably. This action may be prevented by the addition of an appropriate amount of ethylenediaminetetraacetic acid (EDTA), while adsorption at 340nm of NAD is highly increased by the addition of a phosphate buffer solution containing EDTA to an enzyme reaction mixture containing an amino acid, e.g., glycine, thereby causing non-enzymatic change in NAD. Similar change to the above may be caused when a glycine buffer solution or an arginine buffer solution is added to an enzyme reaction mixture containing EDTA, which leads to increase in absorption of NAD at 340nm. A guanidine buffer solution does not show such action, but the solution itself may increase absorption of NAD at the concentration and pH value to inhibit an action of an enzyme. Such increasing action on absorption of NAD may continuously vary with the lapse of time and it is, therefore, difficult to correct influence caused therefrom.

2. INHIBITORY ACTION OF CAPS BUFFER SOLUTION ON DEHYDROGENASE REACTION

Four enzymes which are widely employed for examination in clinical diagnosis among various serum enzymes, were tested on the inhibitory actions by CAPS buffer solution. Some of our experiments are summarized in the Table 1 wherein changes in absorbance at 340nm during the whole process of the reaction are automatically recorded and expressed in terms of inhibition degree by adding serum to a reaction mixture for proceeding the reaction and then adding thereto CAPS buffer solution with varied concentrations, pH values and amounts added.

of coenzyme at 340nm to some extent, though more or less differences may be observed upon the concentration and pH of the buffer solution. However, increases in absorbance of oxidized form and reduced form of coenzyme are approximately equal per unit $\mu$ mole and, accordingly, when working curves are made up by measuring absorbance at 340nm at varied ratios of the oxidized form to the reduced form where a total amount of coenzyme is kept constant, there is obtained a working curve, in case of the addition of CAPS buffer solution, which has a slope equal to that obtained without any addition of the buffer and a shape transferred in parallel with upwards by increased absorption intensity.

In ultraviolet assay method, an enzyme activity is to be determined from differences in absorbance at 340nm before and after reaction proceeding and, therefore, an absorption increasing effect by CAPS buffer solution is eliminated.

ii. Influence upon stability of absorption intensity

As stated above, we have found that absorption of coenzyme at 340nm is increased to some extent upon dissolution by the addition of CAPS buffer solution according to this invention. Some of our experiments about stability of absorption after dissolution are summarized in Table 2 which shows changes in absorption intensity at 340nm over 3 hours after dissolution of coenzyme in CAPS buffer solution.

Table 1

| | CAPS buffer soln. | | Serum enzyme 1) | | | |
|---|---|---|---|---|---|---|
| Amount added 2) | Concentration (M) 3) | PH 3) | GOT | GPT | ALD | CPK |
| ½ Vol. | 0.5 | 12.0 | C 4) | C | C | C |
| | | 12.5 | C | C | C | C |
| | 1 | 11.0 | 80 | C | C | C |
| | | 11.5 | C | C | C | C |
| | 2 | 10.5 | 65 | C | C | C |
| | | 11.0 | C | C | C | C |
| 1 Vol. | 0.5 | 11.0 | 85 | C | C | C |
| | | 11.5 | C | C | C | C |
| | 1 | 10.5 | 70 | C | C | C |
| | | 11.0 | C | C | C | C |
| | 2 | 10.5 | C | C | C | C |
| 2 Vol. | 0.1 | 11.0 | 10 | 70 | 95 | 95 |
| | | 11.5 | 35 | C | C | C |
| | 0.125 | 11.5 | 80 | C | C | C |
| | 0.5 | 10.5 | 85 | C | C | C |
| | | 11.0 | C | C | C | C |
| 4 Vol. | 0.1 | 11.5 | C | C | C | C |
| | 0.125 | 11.0 | C | C | C | C |
| Complete inhibition concentration with aqueous NaOH soln. (Final concentration) | | | >0.15N | >0.15N | >0.1N | >0.1N |

1) Diagnostic kits available from Calbiochem U.S.A., used for measuring GOT, GPT and CPK and diagnostic kits available from Boeringer-Manheim, West Germany, used for measuring ALD, standard human serum (Caltrol-Abnormal) available from Calbiochem used for serum.
2) Volume ratio of the added buffer solution to the enzyme reaction mixture. For instance, ½ volume is meant to show that ½ volume is added per volume of the reaction mixture.
3) Concentration and pH of the added buffer solution.
4) C represents 100 % complete inhibition and figure (%) represents partial inhibition.

3. INFLUENCE OF ADDITION OF CAPS BUFFER SOLUTION UPON ABSORPTION INTENSITY AND ITS STABILITY OF COENZYME AT 340nm i. Influence upon absorption intensity By the addition of CAPS buffer solution to a coenzyme solution is usually increased absorption intensity

Table 2

| CAPS [1] buffer solution | NAD | NADH | NADP | NADPH |
|---|---|---|---|---|
| 0.5M, pH11.5 | 0.010A/hr/cm [2] O.D. change not more than | not changed | not changed | not changed |
| 0.33M, pH11.5 | 0.005A/hr/cm O.D. change not more than | " | " | " |
| 0.25M, pH11.5 | not changed [3] | " | " | " |
| 0.25M, pH11.5 (containing 12.5mM EDTA) | not changed [3] | " | " | " |
| 0.25M, pH12.0 | 0.005A/hr/cm O.D. change not more than | " | " | " |
| 0.25M, pH12.5 | 0.010A/hr/cm O.D. change not more than | " | 0.005A/hr/cm O.D. change not more than | " |

1) Coenzyme dissolved in the indicated buffer solution to $1.1 \times 10^{-4}$ M.
2) Change in absorbance per hour given when measured by the use of a cell with optical path length of 1 cm.
3) Changes in absorbance of ±0.002A or less over 3 hours immediately after dissolution are expressed as "not changed".

As seen from Table 2, all coenzymes are stable in buffer solutions having a concentration of 0.25M or less and a pH value of 11.5 or less and also stable when EDTA contained at 12.5 mM or less. On the other hand, when the concentration is 0.33M or more or pH is 12 or higher, stability of NAD is somewhat reduced and, when pH is 12.5 or higher, stability of NADP is also reduced, whereas stability of a reduced form of coenzyme is not influenced.

If NAD or NADP is dissolved in an aqueous solution of a strong alkali, e.g., sodium hydroxide or potassium hydroxide, absorption intensity at 340nm is increased with the lapse of time to a peak after 10 – 20 minutes and then gradually decreased. Such changes continuously occur over several hours and the higher an alkali concentration is, the greater change is. It is, therefore, extremely difficult to find out such a condition that an enzyme reaction is stopped without any influence upon absorption of coenzyme, when an aqueous solution of a strong alkali having no buffer action is employed.

4. INFLUENCE UPON SERUM TURBIDITY

In determining an enzyme activity, absorbance before reaction is ordinarily measured by adding serum to reaction mixture and immediately adding CAPS buffer solution for reaction stopping. However, the following convenient technique may be utilized by simplifying the above-mentioned procedures, since the addition of CAPS buffer solution does not affect turbidity of the serum.

Absorbance of the reaction medium having CAPS buffer solution incorporated therein is determined beforehand and then absorbance of serum at 340nm is added thereto, thereby absorbance before reaction being defined. According to this technique, saving of reagents is feasible, since reagents are not wasted for every serum in order to determine absorbance before reaction.

In practising the present invention, the concentration of CAPS in its aqueous alkali solution should be within a range of 0.1 – 2M, preferably 0.1 – 0.5M and most preferably 0.5M. The pH value of the CAPS aqueous alkali solution should also be within a range of 10.5 – 12.5, preferably 11.5 – 12.5 and most preferably 11.5. As the alkali which may be employed in this invention, there may be mentioned, for example, alkali metal hydroxides, e.g., potassium hydroxide, sodium hydroxide, lithium hydroxide; ammonium hydroxide and the like. It is to be noted that other alkaline substances than the above may be utilized, provided that they do not adversely affect the assay conditions, the assay results and the like.

It is desirable that a water-miscible aliphatic alcohol is further added to an aqueous alkali solution of CAPS. As the alcohol which may be employed in this invention, there may be mentioned, for example, methanol, ethanol, n-propanol, isopropanol and the like. An amount of the alcohol to be added is not essential feature, but it is usual and preferable to use the alcohol in an amount of 10 – 30% (v/v). Generally, methanol or ethanol may be practically used in an amount of 30%, 10% for n-propanol and 20% for isopropanol being used respectively.

This invention will be concretely illustrated by the following examples, but they are not limiting the scope thereof.

EXAMPLE 1

Measurement of GOT activity in serum a. Two test tubes A and B were used for one serum sample. A reaction mixture (pH 7.4) containing the following ingredient at the indicated amount was poured into each test tube in 1.0 ml. portion.

In units of the values as shown below, an enzyme preparation and other ingredients are indicated in terms of international unit and $\mu$ mole, respectively.

| | |
|---|---|
| Tris(hydroxymethyl)aminomethane | 100 |
| α-Ketoglutaric acid | 7.5 |
| L-Aspartic acid | 36 |
| Succinic acid | 16 |
| Sodium hydrogencarbonate | 0.8 |
| Reduced form of nicotinamide-adenine.dinucleotide | 0.17 |
| Malic acid dehydrogenase | 0.33 unit |
| Lactic acid dehydrogenase | 0.33 unit |

The test tubes were incubated in a water incubator at 30° C. and, after 5 minutes, 25 $\mu l$. of serum was added into the one test tube A and well mixed. After subsequent incubation for 60 minutes, each 1.0 ml. of 0.5M — CAPS buffer solution (pH 11.5) was added into the both test tubes A and B and then 25 μl. of serum was added into the test tube B. Two test tubes were thorougly shaken. Within 3 hours after addition of the CAPS buffer solution, absorbance of the solution in the respective tubes A and B was measured at 340nm by means of a cell with an optical path length of 1 cm.

GOT activity was calculated according to the following equation.

The absorbance of the solution in the test tube A is defined as A and that in the test tube B as B.

(B-A) × 217 = milliunit (international unit)/ml. of serum b. Following the same procedures as in the above (a) except that a 0.2M — CAPS — 30% (v/v) methanol buffer solution (pH 11.5) was employed instead of the 0.5M CAPS buffer solution, there can be obtained similar results.

EXAMPLE 2

Measurement of GPT activity in serum a. Two test tubes A and B were used for one serum sample. A reaction solution (pH 7.4) having the following formulation was poured into each test tube in 1.0 ml. portion. Units for the values are as defined in Example 1 (a).

| | |
|---|---|
| Tris(hydroxymethyl)aminomethane | 100 |
| α-Ketoglutaric acid | 8.17 |
| L-Alanine | 16.5 |
| Succinic acid | 35 |
| Sodium hydrogencarbonate | 0.8 |
| Reduced form of nicotinamide-adenine.dinucleotide | 0.17 |
| Lactic acid dehydrogenase | 0.33 unit |

The test tubes were incubated in a water incubator at 30° C. and the subsequent procedures were carried out in the same manner as in Example 1 (a). GPT activity was calculated by using the same equation as in Example 1 (a).

b. Following the same procedures as in the above (a) except that a 0.2M — CAPS — 20%(v/v) isopropanol buffer solution (pH 11.5) was employed instead of the 0.5M CAPS buffer solution, there can be obtained similar results.

EXAMPLE 3.

Measurement of ALD activity in serum a. Two test tubes A and B were used for one serum sample. A reaction solution (pH 7.4) containing the following formulation was poured into each test tube in 1 ml. portion. Units of the values are as defined in Example 1 (a).

| | |
|---|---|
| Collidine buffer | 56 |
| Monoiodoacetic acid | 0.3 |
| Fructose-1,6-diphosphoric acid | 3 |
| Reduced form of nicotineamide-adenine.dinucleotide | 0.17 |
| Glycerol-1-phosphoric acid dehydrogenase | 0.35 unit |
| Triose phosphate isomerase | 2 units |

Test tubes were incubated in an incubator at 30° C. and, after 5 minutes, 30 μl. of serum was added into the test tube A and well mixed. After incubation for 60 minutes, each 1 ml. of 0.5M — CAPS buffer solution (pH 11.5) was added into the test tubes A and B and then 30 μl. of serum was added into the test tube B. Both test tubes were thoroughly shaken and absorbance was measured at 340nm.

The respective absorbances are defined as A and B and activity is calculated according to the following equation.

(B-A) × 90.6 = milliunit/ml. of serum b. Following the same procedures as in the above (a) except that a 0.2M — CAPS — 10%(v/v) n-propanol buffer solution (pH 11.5) was employed instead of the 0.5M CAPS buffer solution, there can be obtained similar results.

EXAMPLE 4

Measurement of CPK activity in serum

Two test tubes were used for one serum sample and 1 ml. of a reaction solution (pH 7.4) of the following formulation was poured into the respective tubes. Units for the values are as defined in Example 1 (a).

| | |
|---|---|
| N,N'-Bis(2-ethanesulfonic acid)piperazine sodium salt | 50 |
| Sodium carbonate | 20 |
| Disodium creatinephosphate | 20 |
| Trilithium adenosine-5'-diphosphate | 1.5 |
| Glucose | 15 |
| Magnesium aspartate | 10 |
| Adenosine-5'-phosphoric acid | 10 |
| Glutathione | 8.7 |
| Tetrasodium ethylenediaminetetraacetate | 1.66 |
| Oxidized form of nicotineamide-adenine.dinucleotide phosphate | 0.6 |
| Hexokinase | 1 unit |
| Glucose-6-phosphoric acid dehydrogenase | 0.33 unit |

Test tubes were incubated in a water incubator at 30° C. for 5 minutes and then each 50 μl. of serum was added into the test tubes A and B and mixed. Incubation was continued and, after 15 minutes and 60 minutes, each 2 ml. of 0.1M — CAPS — 5 mM EDTA buffer solution (pH 11.5) was added to the test tubes A and B, respectively, to cease the reaction proceedings. The period of time when absorbance at 340nm is to be measured after addition of the CAPS buffer solution, is arranged to be substantially the same with regard to both test tubes A and B.

Absorbances of the liquids in test tubes A and B are defined as A and B, respectively, and an activity is calculated according to the following formula.

(A-B) × 218 = milliunit/ml. of serum

What is claimed is:

1. A method for stopping an enzyme reaction of a dehydrogenase or a dehydrogenase system in a spectrophotometric assay method of an activity of serum enzyme in said enzyme or enzyme system which comprises applying as a stopping agent for said enzyme reaction an aqueous alkali solution of cyclohexylaminopropanesulfonic acid having a concentration of 0.1 – 2M and a pH value of 10.5 – 12.5.

2. A method according to claim 1 wherein said assay method is effected by measuring a change in absorbance at 340nm of nicotinamide adenine dinucleotide or nicotinamide adenine dinucleotide phosphate.

3. A method according to claim 2 wherein said aqueous alkali solution further contains a water-miscible aliphatic alcohol.

4. A method according to claim 3 wherein said alcohol is methanol, ethanol, n-propanol or isopropanol.

5. A method according to claim 3 wherein said alcohol is contained in an amount of 10 to 30%.

6. A method according to claim 3 wherein said alcohol is isopropanol and said isopropanol is contained in an amount of 20%.

7. A method according to claim 3 wherein said concentration is 0.2M, said pH value is 11.5 and said alcohol is isopropanol in an amount of 20%.

8. A method according to claim 3 wherein said alcohol is methanol or ethanol in an amount of 30%.

9. A method according to claim 3 wherein said alcohol is n-propanol in an amount of 10%.

10. A method according to claim 2 wherein said concentration is 0.1 – 0.5M and said pH value is 11.5 – 12.5.

11. A method according to claim 2 wherein said concentration is 0.5M and said pH value is 11.5.

12. A method according to claim 1 wherein said assay method is effected by measuring a change in fluorescence intensity with exciting light of 340nm of nicotinamide adenine dinucleotide or nicotinamide adenine dinucletide phosphate.

13. A method according to claim 12 wherein said aqueous alkali solution further contains a water-miscible aliphatic alcohol.

14. A method according to claim 13 wherein said alcohol is methanol, ethanol, n-propanol or isopropanol.

15. A method according to claim 13 wherein said alcohol is contained in an amount of 10 to 30%.

16. A method according to claim 13 wherein said alcohol is isopropanol and said isopropanol is contained in an amount of 20%.

17. A method according to claim 13 wherein said concentration is 0.2M, said pH value is 11.5 and said alcohol is isopropanol in an amount of 20%.

18. A method according to claim 13 wherein said alcohol is methanol or ethanol in an amount of 30%.

19. A method according to claim 13 wherein said alcohol is n-propanol in an amount of 10%.

20. A method according to claim 12 wherein said concentration is 0.1 – 0.5M and said pH value is 11.5 – 12.5.

21. A method according to claim 12 wherein said concentration is 0.5M and said pH value is 11.5.

22. A method according to claim 1 wherein said aqueous alkali solution further contains a water-miscible aliphatic alcohol.

23. A method according to claim 1 wherein said concentration is 0.1 – 0.5M and said pH value is 11.5 – 12.5.

24. A method according to claim 1 wherein said concentration is 0.5M and said pH value is 11.5.

* * * * *